United States Patent [19]

Miyoshi et al.

[11] Patent Number: 4,635,027
[45] Date of Patent: Jan. 6, 1987

[54] RESISTANCE-VARIATION TYPE MOISTURE SENSOR

[75] Inventors: Shuji Miyoshi; Masaya Hijikigawa, both of Nara, Japan

[73] Assignee: Sharp Kabushiki Kaisha, Osaka, Japan

[21] Appl. No.: 761,494

[22] Filed: Aug. 1, 1985

[30] Foreign Application Priority Data

Aug. 28, 1984 [JP] Japan .................................. 59-181287

[51] Int. Cl.[4] ............................................. H01R 13/44
[52] U.S. Cl. ........................................ 338/34; 338/35; 427/101
[58] Field of Search .................... 338/35, 34; 427/171, 427/173, 174, 101; 428/172, 148

[56] References Cited

U.S. PATENT DOCUMENTS 4,439,479  3/1984  Kanai et al. ..................... 428/172 X
4,473,813  9/1984  Kinjo et al. ............................ 338/35
4,492,719  1/1985  Kanai et al. ..................... 427/174 X Primary Examiner—E. A. Goldberg
Assistant Examiner—M. M. Lateef
Attorney, Agent, or Firm—Spencer & Frank

[57] ABSTRACT

A resistance-variation type moisture sensor comprising a moisture sensitive film made of a moisture sensitive material which consists essentially of sodium styrenesulfonate, methylene-bis-acrylamide, polyvinyl alcohol and polyethylene glycol, said polyethylene glycol being contained in the moisture sensitive film in an amount ranging from 3 to 7 parts by weight per 100 parts by weight of sodium styrenesulfonate.

2 Claims, 5 Drawing Figures

Amount of PEG / 100 Parts by Weight of NaSS in Moisture Sensitive Film

RESISTANCE-VARIATION TYPE MOISTURE SENSOR

BACKGROUND OF THE INVENTION

1. Field of the Invention

This invention relates to a resistance-variation type moisture sensor comprising a moisture sensitive film of a polyelectrolyte, which detects variation of humidity in the atmosphere by means of a variation in the resistance of the moisture sensitive film based on the water-molecular absorption or the water-molecule desorption thereof.

2. Description of the Prior Art

As a moisture sensitive material wherein electrical resistance or electrical capacitance varies depending upon a variation in humidity or water vapor in the atmosphere, there have been, for example, a moisture sensitive material having a sintered body of metal oxides such as iron oxide ($Fe_2O_3$ or $Fe_3O_4$), tin oxide ($SnO_2$), etc., or a metal oxide film; a moisture sensitive material having a hydrophilic polymer film or a polyelectrolyte; a moisture sensitive material having an electrolyte salt such as lithium chloride (LiCl); and a moisture sensitive material having a hygroscopic polymer film in which conductive particles or fibers such as carbon are dispersed.

While moisture sensors containing a metal oxide film or a polyelectrolyte film generally have a wide moisture-sensitivity range, their resistance varies exponentially, responding to relative humidity in the atmosphere. Moisture sensors containing a metal oxide have an excellent heat resistance and respond rapidly, but they have a high temperature resistance coefficient. Especially, moisture sensors having a sintered body of metal oxides are inferior in reproducibility and/or interchangeability of the moisture sensitive characteristic thereof because the moisture sensitive characteristic depends upon the constituents of the sensor to a great extent. Moisture sensors having an electrolyte salt such as lithium chloride detect only humidity in a narrow range and if they are allowed to stand in a highly humid atmosphere for a long period of time, the electrolyte salt therein is eluted or diluted resulting in deterioration of the moisture sensitive characteristic of the sensor, and accordingly it cannot be used for the determination of high humidity. Moisture sensors having a hygroscopic resin or the like, in which conductive particles or fibers are dispersed, cannot detect a humidity in a wide range because they exhibit a steep variation of the resistance thereof in a highly humid atmosphere, while it is not sensitive to low humidity. Also a moisture sensor having a hydrophilic polymer film or a polyelectrolyte film is inferior in moisture resistance, water resistance and durability, so that if it were allowed to stand in a highly humid atmosphere or in dew for a long period, its moisture sensitive characteristic would be changed, while it is advantageous in that it operates in a wide moisture sensitive range, has a rapid moisture sensitive response, a simple structure, and is easily produced at a low cost. A moisture sensor having a hydrophilic polymer film or a polyelectrolyte film is also inferior in heat-resistance, so that if it were allowed to stand at a high temperature (e.g., 100° C.), its moisture sensitive characteristic would deteriorate and/or change.

SUMMARY OF THE INVENTION

The resistance-variation type moisture sensor of this invention which overcomes the above-discussed and numerous other disadvantages and deficiencies of the prior art, comprises a moisture sensitive film made of a moisture sensitive material which consists essentially of sodium styrenesulfonate, methylene-bis-acrylamide, polyvinyl alcohol and polyethylene glycol, said polyethylene glycol being contained in the moisture sensitive film in an amount ranging from 3 to 7 parts by weight per 100 parts by weight of sodium styrenesulfonate.

The moisture sensitive film is, in a preferred embodiment, prepared by coating said moisture sensitive material on a substrate containing a pair of comb-shaped electrodes thereon, and then subjecting the resulting coated film to an ultraviolet radiation treatment to allow the polymerization of sodium styrenesulfonate therein and simultaneously the cross-linkage of the sodium styrenesulfonate by methylene-bis-acrylamide, resulting in said moisture sensitive film having a network structure.

Thus, the invention described herein makes possible the objects of (1) providing a resistance-variation type moisture sensor which exhibits an excellent moisture resistance and an excellent water resistance; (2) providing a resistance-variation type moisture sensor which exhibits an excellent heat resistance and an excellent stable moisture sensitive characteristic even if it is allowed to stand in a high temperature atmosphere for a long period; and (3) providing a resistance-variation type moisture sensor which also exhibits relatively small resistance values, in addition to the above-mentioned characteristics, so that it is suitable for practical use.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
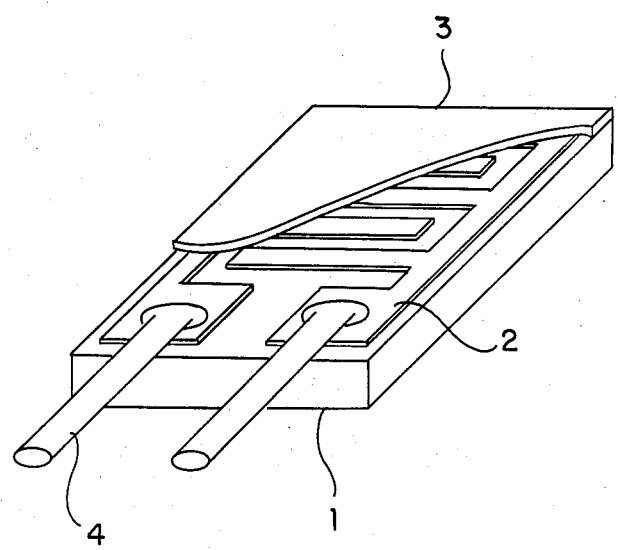
FIG. 1 is a partially cutaway view illustrating a resistance-variation type moisture sensor manufactured for evaluation of the moisture sensitive characteristic (i.e., the relationship between the resistance and the relative humidity) with respect to a resistance-variation type moisture sensor of this invention.

FIG. 1 shows a resistance-variation type moisture sensor of this invention, which is produced as follows: On a highly insulating substrate 1 such as alumina, glass, etc., a pair of comb-shaped conductive metal films 2 made of gold, etc., are formed as a pair of electrodes by a vacuum evaporation technique, a sputtering method, etc., followed by the formation of a moisture sensitive film 3 thereon, which is composed of specific components specified below, the resistance of which varies depending upon humidity in the atmosphere. Lead wires 4 were then connected to the end portions of the comb-shaped electrodes 2, respectively, resulting in a resistance-variation type moisture sensor of this invention.

When a conventional moisture sensor having a moisture sensitive film of a linear polyelectrolyte is allowed to stand in a highly humid atmosphere or in dew, the moisture sensitive film therein swells and/or is eluted, resulting in great deterioration of the moisture sensitive characteristic of the sensor. The swelling and elution of the moisture sensitive film can be avoided by cross-linking the polyelectrolyte constituting the moisture sensitive film, creating a moisture sensitive film having a network structure (i.e., a three-dimensionally cross-linked structure), resulting in a resistance-variation type moisture sensor having a resistance to humidity and water.

The heat resistance of a resistance-variation type moisture sensor depends upon the chemical and structural thermostability of the moisture sensitive material of the moisture sensitive film. Since the moisture sensitive film swells due to water-absorption, the structural thermostability of the moisture sensitive film depends upon the hygroscropic characteristic of the moisture sensitive film itself, and accordingly, the moisture sensitive film becomes thermally stable as its hygroscopicity is reduced. However, when the hygroscopicity of the moisture sensitive film is reduced too much, the amount of water to be absorbed into the moisture sensitive film becomes small resulting in an increase in the resistance of the resulting moisture sensor, causing great inconvenience in practical use. In order to obtain a resistance-variation type moisture sensor exhibiting resistance in a limited range and having moisture sensitive characteristics which are stable even when the sensor is left in a high temperature and arid atmosphere, a substance which reduces the hygroscopicity of the moisture sensitive film and suppresses the increase in the electrical resistance of the resulting sensor must be contained in the moisture sensitive film. In this invention, polyethylene glycol is used as such a substance.

Then, 1 g of sodium styrenesulfonate as a monomer, 0.05 g of methylene-bis-acrylamide and 0.2 g of polyvinyl alcohol, both of which serve as a cross-linking agent, are dissolved in 5 ml of water and coated on the substrate 1 having a pair of the comb-shaped metal films 2 thereon, followed by an ultraviolet radiation treatment in a nitrogen atmosphere to form a moisture sensitive film 3. Then, lead wires 4 are connected to the end portions of the comb-shaped metal films, respectively, which are exposed, to form a pair of electrodes, resulting in the resistance-variation type moisture sensor shown in FIG. 1.

Due to ultraviolet radiation applied to the coated film, sodium styrenesulfonate contained therein is polymerized and simultaneously cross-linked by methylene-bis-acrylamide contained therein, resulting in a moisture sensitive film having a network structure.

Figure 2:
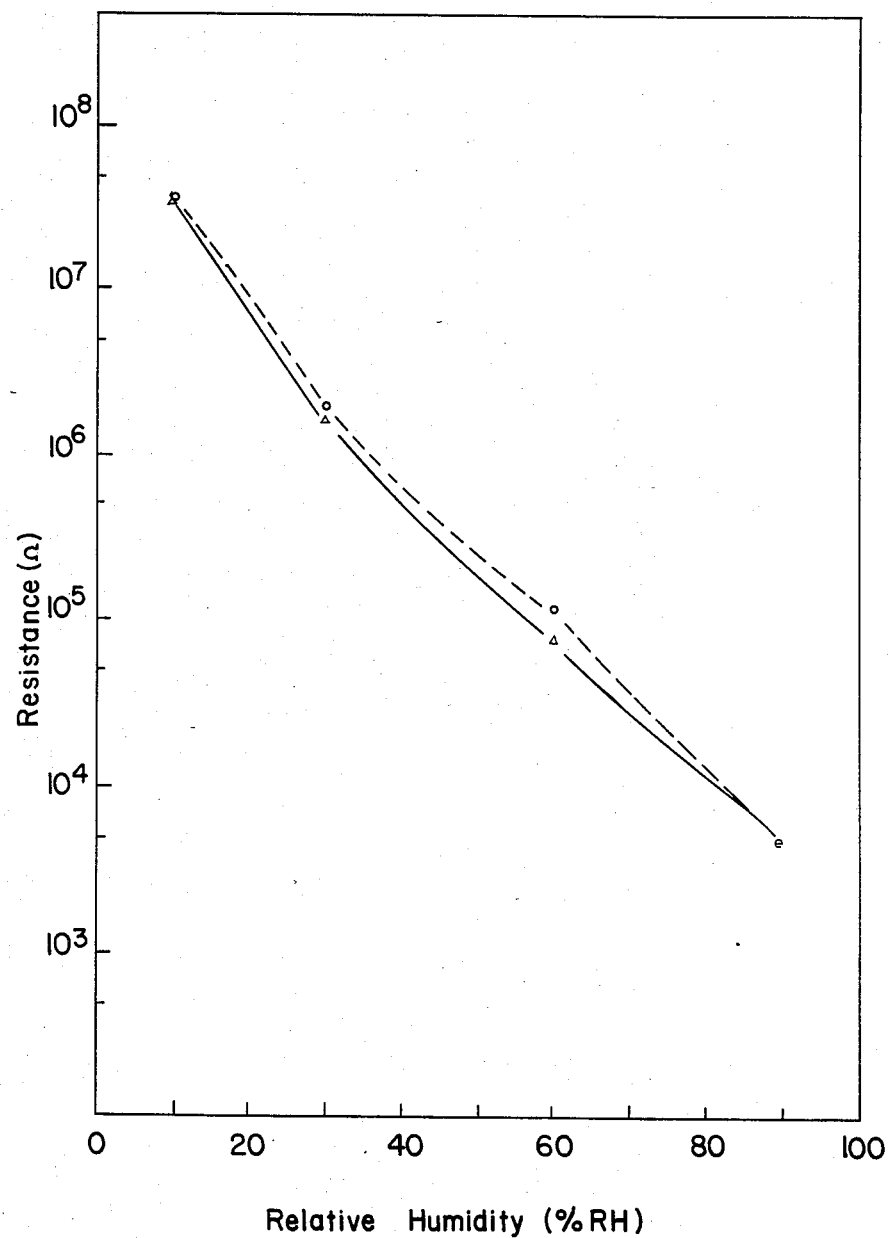
FIG. 2 is graph showing the moisture sensitive characteristic of a resistance-variation type moisture sensor which does not contain polyethylene glycol.

FIG. 2 shows the moisture sensitive characteristics (i.e., the relationship between the resistance and the relative humidity) of a resistance-variation type moisture sensor as a reference control sensor, which was manufactured, in the same manner as in the above-mentioned sensor of this invention in FIG. 1, except that polyethylene glycol was not contained in the moisture sensitive film therein. The curves represented by the solid line and the dotted line, respectively, show the moisture sensitive characteristics before and after the sensor was allowed to stand at a high temperature of 100° C. for 15 hours. Upon completion of the first measurement of the moisture sensitive characteristic of the sensor after the sensor was left at 100° C. for 15 hours, the second measurement was carried out and the same characteristic curve as represented by the solid line in FIG. 2 was obtained. This indicates that when a reference control sensor having a moisture sensitive film which does not contain polyethylene glycol therein is allowed to stand at a high temperature of 100° C. for a certain period of time, its moisture sensitive characteristic temporarily varies, resulting in a difference of 4.2%RH (which is based on the relative humidity) in a relative humidity of 60% measured therebefore and thereafter.

EXAMPLE 1

One gram of sodium styrenesulfonate, 0.05 g of methylene-bis-acrylamide and 0.2 g of polyvinyl alcohol were dissolved in 5 ml of water, and 0.2 g of polyethylene glycol was further dissolved therein. The resulting solution was coated on a alumina substrate 1, on which a pair of gold electrodes 2 were formed into the comb-shaped pattern, and subjected to an ultraviolet radiation treatment in a nitrogen atmosphere to form a moisture sensitive film 3. Lead wires 4 were then connected to the end portions of the comb-shaped gold electrodes 2 which were exposed, resulting in the resistance-variation type moisture sensor shown in FIG. 1. Then, the moisture sensitive characteristics of the sensor, before and after the sensor was allowed to stand at a high temperature of 100° C. for 15 hours, were measured, respectively. The difference in the relative humidity of 60% measured therebefore and thereafter was 1.2%RH, which was based on the relative humidity. While the difference of 1.2%RH is small and within the perimeters of experimental error to be acceptable for the practical use, the resistance of the sensor in a relative humidity of 30% is as high as $3.8 \times 10^7 \Omega$, which causes difficulty for the practical use of the sensor, as compared with that of the reference control sensor containing no polyethylene glycol which was as small as $2.5 \times 10^6 \Omega$.

EXAMPLE 2

One gram of sodium styrenesulfonate, 0.05 g of methylene-bis-acrylamide, 0.2 g of polyvinyl alcohol and 0.1 g of polyethylene glycol were dissolved in 5 ml of water and then coated on an alumina substrate on which a pair of gold electrodes 2 were formed into the comb-shaped pattern, followed by an ultraviolet radiation treatment in a nitrogen atmosphere to form a moisture sensitive film 3. Then, lead wire 4 were connected to the end portions of the comb-shaped electrode 2 which were exposed, resulting in a resistance-variation type moisture sensor in FIG. 1. Then, the moisture sensitive characteristics of the sensor, before and after the sensor was allowed to stand at a high temperature of 100° C. for 15 hours, were measured, respectively. The difference in the relative humidity of 60% therebetween was 1.2%RH which was based on the relative humidity. While the difference of 1.2%RH is small and within the perimeters of experimental error to be acceptable for the practical use, the resistance of the sensor in a relative humidity of 30% was as high as $1.4 \times 10^7 \Omega$.

EXAMPLE 3

Figure 3:
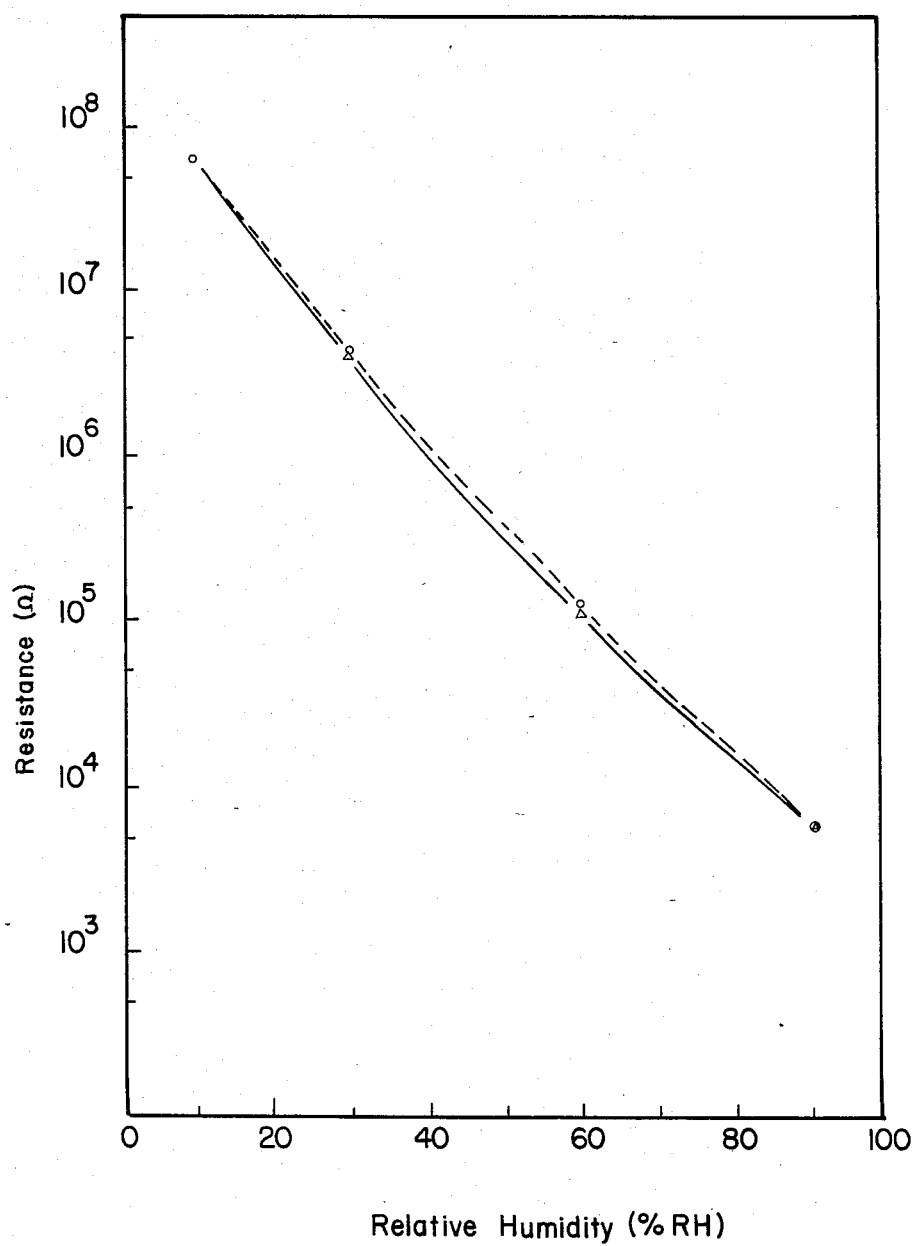
FIG. 3 is graph showing the moisture sensitive characteristic of a resistance-variation type moisture sensor which contains polyethylene glycol in an amount of 5 parts by weight per 100 parts by weight of sodium styrenesulfonate.

One gram of sodium styrenesulfonate, 0.05 g of methylene-bis-acrylamide, 0.2 g of polyvinyl alcohol and 0.05 g of polyethylene glycol were dissolved in 5 ml of water and used to form a moisture sensitive film 3, in the same manner as the above-mentioned Examples, resulting in the resistance-variation type moisture sensor in FIG. 1. The moisture sensitive characteristics of this sensor are shown in FIG. 3, wherein the curves representing by the solid line and the dotted line, respectively, show the moisture sensitive characteristics before and after the sensor was allowed to stand at a high temperature of 100° C. for 15 hours, and indicate that a difference in the relative humidity of 60% therebetween is as small as 1.3%RH (which is based on the relative humidity). Moreover, the resistance of the sensor in a relative humidity of 30% was as small as $3.5 \times 10^6 \Omega$.

EXAMPLE 4

One gram of sodium styrenesulfonate, 0.05 g of methylene-bis-acrylamide, 0.2 g of polyvinyl alcohol and 0.025 g of polyethylene glycol were dissolved in 5 ml of water, and used to form a moisture sensitive film 3 in the same manner as the above-mentioned, resulting in the resistance-variation type moisture sensor in FIG. 1. While the resistance of this sensor in a relative humidity of 30% was as small as $3.0 \times 10^6 \Omega$, the moisture sensitive characteristics thereof, before and after the sensor was left at a high temperature of 100° C. for 15 hours, were quite different from each other, the difference in the relative humidity of 60% therebetween being as great as 2.8%RH (which is based on the relative humidity).

Figure 4:
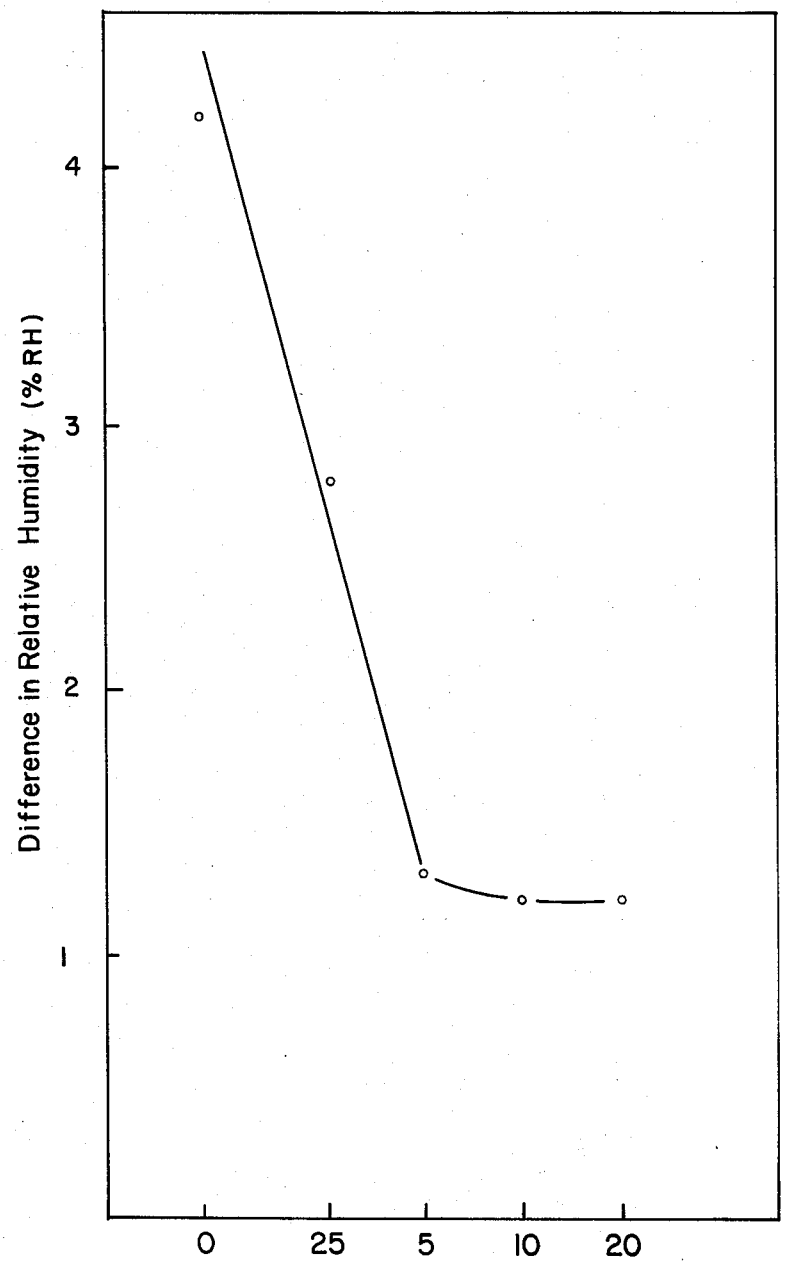
FIG. 4 is a graph showing the relationship between the amount of polyethylene glycol contained in a moisture sensor and the difference in the relative humidity of 60% measured before and after the moisture sensor was allowed to stand at a high temperature.
Figure 5:
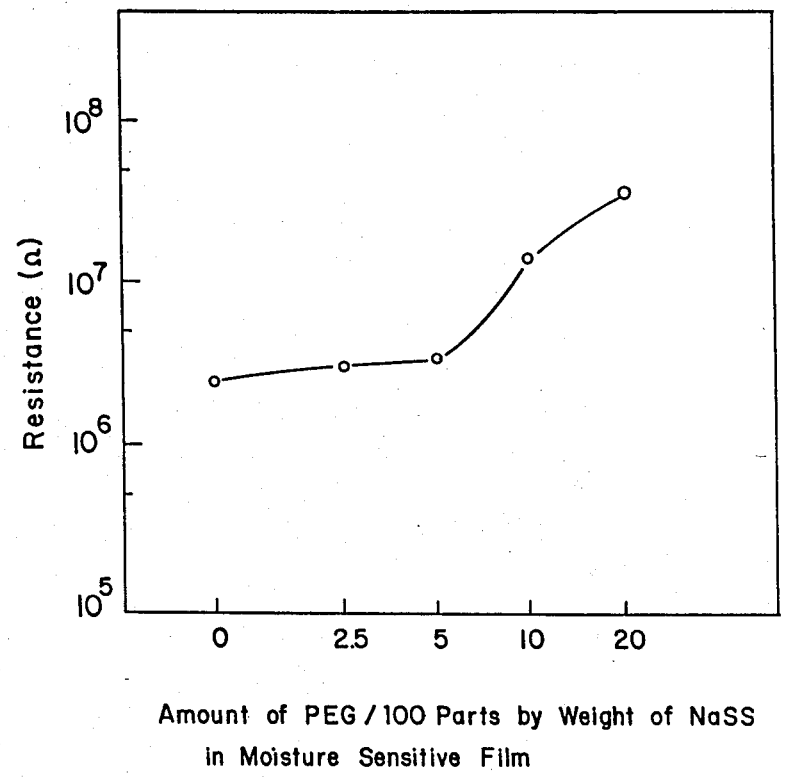
FIG. 5 is a graph showing the relationship between the amount of polyethylene glycol contained in a moisture sensor and the resistance of the moisture sensor in a relative humidity of 30%.

As seen from the above-mentioned Examples, when a resistance-variation type moisture sensor containing polystyrene sulfonate is allowed to stand in a high temperature and arid atmosphere for a long period, the resistance thereof temporarily varies. The extent of the variation of the resistance can be reduced by the use of polyethylene glycol in the moisture sensitive film. Since the use of polyethylene glycol allows an increase in the resistance of the sensor, the amount thereof must be limited to a given range. FIGS. 4 and 5, which respectively show the relationship between the amount of polyethylene glycol contained in the moisture sensitive film and the temporary difference in a relative humidity of 60% before and after the sensor was allowed to stand in a high temperature and arid atmosphere, and the relationship between the amount of polyethylene glycol contained in the moisture sensitive film and the resistance of the sensor, indicate that the amount of polyethylene glycol to be contained in the moisture sensitive film is preferably in the range of 3 to 7 parts by weight per 100 parts by weight of sodium styrenesulfonate, more preferably 5 parts by weight per 100 parts by weight of sodium styrenesulfonate.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A resistance-variation type moisture sensor comprising a moisture sensitive film made of a moisture sensitive material which consists essentially of sodium styrenesulfonate, methylene-bis-acrylamide, polyvinyl alcohol and polyethylene glycol, said polyethylene glycol being contained in the moisture sensitive film in an amount ranging from 3 to 7 parts by weight per 100 parts by weight of sodium styrenesulfonate.

2. A resistance-variation type moisture sensor according to claim 1, wherein said moisture sensitive film is prepared by coating said moisture sensitive material on a substrate containing a pair of comb-shaped electrodes thereon, and then subjecting the resulting coated film to an ultraviolet radiation treatment to allow the polymerization of sodium styrenesulfonate therein and simultaneously the cross-linkage of the sodium styrenesulfonate by methylene-bis-acrylamide, resulting in said moisture sensitive film having a network structure.

* * * * *